(12) United States Patent
Flockerzi

(10) Patent No.: US 6,436,952 B1
(45) Date of Patent: Aug. 20, 2002

(54) BENZONAPHTHYRIDINE-N-OXIDES COMPRISING A PDE3 AND PDE4 INHIBITING ACTIVITY

(75) Inventor: Dieter Flockerzi, Allensbach (DE)

(73) Assignee: BYK Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/744,974

(22) PCT Filed: Aug. 21, 1999

(86) PCT No.: PCT/EP99/06139

§ 371 (c)(1),
(2), (4) Date: Feb. 15, 2001

(87) PCT Pub. No.: WO00/12501

PCT Pub. Date: Mar. 9, 2000

(30) Foreign Application Priority Data

Aug. 31, 1998 (EP) .............................. 98116416

(51) Int. Cl.⁷ .................. A61K 31/4375; C07D 471/04; A61P 11/06; A61P 17/06; A61P 9/12
(52) U.S. Cl. ......................... 514/292; 514/287; 546/65; 546/81
(58) Field of Search ..................... 546/81, 65; 514/292, 514/287

(56) References Cited

U.S. PATENT DOCUMENTS 3,899,494 A    8/1975   Ott et al. ................ 260/287 R
6,008,215 A    12/1999  Flockerzi ..................... 514/212
6,143,759 A  * 11/2000  Flockerzi ..................... 514/292
6,306,869 B1   10/2001  Flockerzi ..................... 514/287

FOREIGN PATENT DOCUMENTS

WO           98/21208         5/1998

OTHER PUBLICATIONS

King FD. Medicinal Chemistry: Principles and Practice. The Royal Society of Chemistry. 1994. pp. 206–209.*

* cited by examiner

*Primary Examiner*—Evelyn Mei Huang
(74) *Attorney, Agent, or Firm*—Jacobson Holman, PLLC

(57) ABSTRACT

Compounds of the formula I,

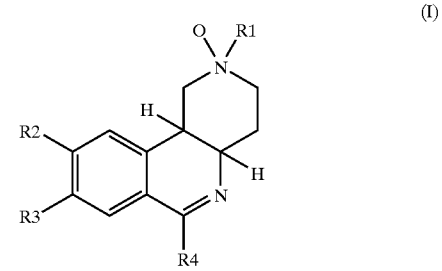

in which R1, R2, R3 and R4 have the meanings indicated in the description, are novel active bronchial therapeutics.

10 Claims, No Drawings

BENZONAPHTHYRIDINE-N-OXIDES COMPRISING A PDE3 AND PDE4 INHIBITING ACTIVITY

This application is the 371 of PCT/EP99/06139, filed on Aug. 21, 1999.

FIELD OF APPLICATION OF THE INVENTION

The invention relates to novel benzonaphthyridine N-oxides which are used in the pharmaceutical industry for the production of medicaments.

KNOWN TECHNICAL BACKGROUND

DE-A 21 23 328 and U.S. Pat. 3,899,494 describe substituted benzonaphthyridines which are distinguished by marked inhibition of blood platelet aggregation. International Applications WO 91/17991 and WO 98/121208 disclose 6-phenylbenzonaphthyridines for the treatment of inflammatory airway disorders.

DESCRIPTION OF THE INVENTION

It has now been found that the following compounds of the formula I which are described in greater detail and differ from the compounds of WO 91/17991 and WO 98/21208, in particular, by the substitution on the 6-phenyl ring and the presence of an N-oxide in the 2-position, have surprising and particularly advantageous properties.

The invention thus relates to compounds of the formula I

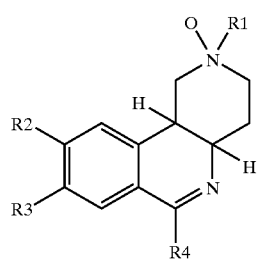

(I)

in which

R1 is 1–4C-alkyl,

R2 is hydroxyl, 1–4C-alkoxy, 3–7C-cycloalkoxy, 3–7C-cycloalkylmethoxy or 1–4C-alkoxy which completely or predominantly substituted by fluorine, R3 is hydroxyl, 1–4C-alkoxy, 3–7C-cycloalkoxy, 3–7C-cycloalkylmethoxy or 1–4C-alkoxy which completely or predominantly substituted by fluorine, or in which R2 and R3 together are a 1–2C-alkylenedioxy group, R4 is a phenyl radical which is substituted by R5, where R5 is a tetrazol-5-yl radical which is substituted by a radical R6, where R6 is hydrogen, 1–10C-alkyl, 3–7C-cycloalkyl, 3–7C-cycloalkylmethyl or Ar-1–4C-alkyl, where Ar is a phenyl radical which is unsubstituted or substituted by R7 and/or R8, and R7 and R8 independently of one another are 1–4C-alkyl or 1–4C-alkoxy, and to the salts of these compounds.

1–4C-Alkyl represents a straight-chain or branched alkyl radical having 1 to 4 carbon atoms. Examples which may be mentioned are the butyl, isobutyl, sec-butyl, tert-butyl, propyl, isopropyl and, preferably, the ethyl and methyl radicals.

1–4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, preferably, the ethoxy and methoxy radicals.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

As 1–4C-Alkoxy which is completely or predominantly substituted by fluorine, the 2,2,3,3,3-penta-fluoropropoxy, the perfluoroethoxy, the 1,2,2-trifluoroethoxy, in particular the 1,1,2,2-tetrafluoroethoxy, the trifluoromethoxy, the 2,2,2-trifluoroethoxy, and preferably the difluoromethoxy radicals, for example, may be mentioned.

1–2C-Alkylenedioxy represents, for example, the methylenedioxy (—O—CH$_2$—O—) or the ethylenedioxy radical (—O—CH$_2$—CH$_2$—O—).

1–10C-Alkyl represents straight-chain or branched alkyl radicals having 1 to 10 carbon atoms. Examples which may be mentioned are the decyl, nonyl, octyl, heptyl, isoheptyl (5-methylhexyl), hexyl, isohexyl (4-methylpentyl), neohexyl (3,3-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3–7C-Cycloalkyl represents the cyclopropyl, cyclobutyl, cyclopentyl, cyclohexyl or cycloheptyl radical. The 5–7C-cycloalkyl radicals cyclopentyl, cyclohexyl and cycloheptyl may preferably be mentioned.

3–7C-Cycloalkylmethyl represents a methyl radical which is substituted by one of the abovementioned 3–7C-cycloalkyl radicals. Examples which may be mentioned are the cyclopentylmethyl and cyclohexyl-methyl radicals.

Ar-1–4C-alkyl is one of the abovementioned 1–4C-alkyl radicals which is substituted by one of the aryl radicals defined above. Examples which may be mentioned are the p-methoxybenzyl, the phenethyl and the benzyl radicals.

Suitable salts of compounds of the formula I—depending on substitution—are all acid addition salts or all salts with bases. The pharmacologically tolerable salts of the inorganic and organic acids and bases customarily used in pharmacy may be particularly mentioned. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxylbenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxyl-2-naphthoic acid, where the acids are employed in salt preparation—depending on whether a mono- or polybasic acid is concerned and depending on which salt is desired—in an equimolar quantitative ratio or one differing therefrom.

On the other hand—for example in the case of 1H- or 2H-tetrazol-5-yl substitution—salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can be obtained first, for example, as process products in the preparation of the compounds according to the invention on an industrial scale, are converted into pharmacologically tolerable salts by methods known to the person skilled in the art.

It is known to the person skilled in the art that the compounds according to the invention and their salts, if they are isolated, for example, in crystalline form, can contain various amounts of solvents. The invention therefore also comprises all solvates and in particular all hydrates of the compounds of the formula I, and also all solvates in particular all hydrates of the salts of the compounds of the formula I.

Compounds of the formula I to be emphasized are those in which

R1 is 1–2C-alkyl,
R2 is 1–4C-alkoxy, 3–7C-cycloalkoxy, 3–7C-cycloalkylmethoxy or 1–4C-alkoxy which is completely or predominantly substituted by fluorine,
R3 is 1–4C-alkoxy, 3–7C-cycloalkoxy, 3–7C-cycloalkylmethoxy or 1–4C-alkoxy which is completely or predominantly substituted by fluorine,
or in which
R2 and R3 together are a 1–2C-alkylenedioxy group,
R4 is a phenyl radical which is substituted by R5, where
R5 is a tetrazol-5-yl radical which is substituted by a radical R6, where
R6 is hydrogen, 1–7C-alkyl, 3–7C-cycloalkyl, 3–7C-cycloalkylmethyl or Ar-1–4C-alkyl,
where
Ar is a phenyl radical which is unsubstituted or substituted by R7 and/or R8, and
R7 and R8 independently of one another are 1–4C-alkyl or 1–4C-alkoxy,
and the salts of these compounds.

Compounds of the formula I particularly to be emphasized are those in which

R1 is methyl,
R2 is 1–4C-alkoxy, 3–7C-cycloalkoxy, 3–7C-cycloalkylmethoxy or 1–2C-alkoxy which is completely or predominantly substituted by fluorine,
R3 is 1–4C-alkoxy, 3–7C-cycloalkoxy, 3–7C-cycloalkylmethoxy or 1–2C-alkoxy which is completely or predominantly substituted by fluorine,
R4 is a phenyl radical which is substituted by R5, where
R5 is a tetrazol-5-yl radical which is substituted by a radical R6, where
R6 is hydrogen, 1–7C-alkyl, 5–7C-cycloalkyl, 3–7C-cycloalkylmethyl or Ar-1–2C-alkyl,
where
Ar is a phenyl radical which is unsubstituted or substituted by R7, and
R7 is 1–2C-alkyl or 1–2C-alkoxy,
and the salts of these compounds.

Preferred compounds of the formula I are those in which

R1 is methyl,
R2 is 1–4C-alkoxy,
R3 is 1–4C-alkoxy,
R4 is a phenyl radical which is substituted by R5, where
R5 is a tetrazol-5-yl radical substituted by a radical R6, where
R6 is hydrogen, 1–7C-alkyl, cyclohexylmethyl or 4-methoxybenzyl,
and the salts of these compounds.

Particularly preferred compounds of the formula I are those in which

R1 is methyl,
R2 is ethoxy,
R3 is methoxy or ethoxy,
R4 is a phenyl radical which is substituted by R5, where
R5 is a tetrazol-5-yl radical substituted by a radical R6, where
R6 is 1–4C-alkyl,
and the salts of these compounds.

The compounds of the formula I are chiral compounds having chiral centers in positions 2, 4a and 10b. The numbering of the compounds of the formula I is shown in formula Ia.

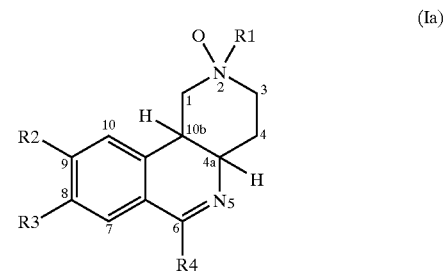

(Ia)

The invention therefore relates to all eight conceivable enantiomers in any desired mixing ratio to one another. The compounds of the formula I are preferred in which the hydrogen atoms in positions 4a and 10b are in the cis position relative to one another.

Particularly preferred in this connection are those compounds of the formula I which in positions 4a and 10b have the same absolute configuration as the compound (–)-cis-4-amino-3-(3-ethoxy-4-methoxyphenyl)-1-methylpiperidine dihydrochloride having the optical rotation $[\alpha]_D^{20}=-65.5°$ (c=1, methanol) which can be employed as a starting material.

The tetrazol-5-yl radical R5 of the compounds of the formula I can be bonded to the phenyl radical R4 in the ortho, meta and also in the para position to the benzonaphthyridine ring.

Preferred compounds of the formula I are those in which the tetrazol-5-yl radical R5 is bonded to the phenyl radical R4 in the meta or para position to the benzonaphthyridine ring. Particularly preferred compounds of the formula I in this connection are those in which the tetrazol-5-yl radical R5 is bonded in the para position.

Compounds of the formula I in which R1, R2, R3, R4 and R5 have the meanings indicated above and R6 is hydrogen occur in a number of tautomeric forms, which are in equilibrium with one another (e.g. the 1H and 2H form of the tetrazol-5-yl radical). The invention comprises all tautomeric forms in any mixing ratio.

By bonding of the substituent R6 (R6≠H) to the tetrazol-5-yl group, the conversion of the two tautomeric 1H and 2H forms of the tetrazol-5-yl radical into one another is blocked. The invention therefore also relates to 1H- and 2H-tetrazol-5-yl compounds of the formula I substituted by a radical R6 (R6≠H), both in pure form and in any mixing ratio. Preferred compounds of the formula I, however, are those in which the tetrazol-5-yl radical in the 2 position is substituted by one of the radicals R6 (R6≠H).

The invention further relates to a process for the preparation of the compounds of the formula I, in which R1, R2, R3 and R4 have the meanings indicated above, and their salts. The process comprises subjecting compounds of the formula II

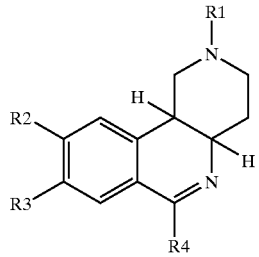

(II)

in which R1, R2, R3 and R4 have the meanings indicated above, to an N-oxidation reaction and, if desired, then converting the compounds of the formula I obtained into their salts, or, if desired, then converting salts of the compounds of the formula I obtained into the free compounds.

The N-oxidation is carried out in a manner familiar to the person skilled in the art, e.g. with the aid of hydrogen peroxide in methanol or with the aid of m-chloroperoxybenzoic acid in dichloromethane at room temperature. The person skilled in the art is familiar on the basis of his/her expert knowledge with the reaction conditions which are specifically necessary for carrying out the process.

Compounds of the formula II in which R1, R2 and R3 have the meanings indicated above, R4 is a phenyl radical substituted by a 1H- or 2H-tetrazol-5-yl radical R5, can be prepared, for example, from the corresponding compounds of the formula II in which R4 is a phenyl radical substituted by a cyano group, by reaction with an alkali metal azide and an ammonium halide (e.g. ammonium chloride). Corresponding reactions are described, for example, in J. Med. Chem. 1993, 36, 3246.

The compounds of the formula II obtained in this way can be converted into further compounds of the formula II, if desired, by an alkylation reaction, the hydrogen on the tetrazol-5-yl radical being replaced by one of the radicals mentioned above for R6 —excluding hydrogen.

The alkylation reactions are expediently carried out analogously to the methods known to the person skilled in the art, e.g. by reaction of the 1H- or 2H-tetrazol compounds of the formula II with compounds of the formula R6-X in the presence of a base, R6 having the abovementioned meanings—excluding hydrogen—and X being a suitable leaving group such as a chlorine, bromine or iodine atom or an alkylsulfate radical. The 1- and 2-substituted tetrazole regioisomer mixtures usually formed in the alkylation are separated by methods known to the person skilled in the art, such as crystallization or chromatography on suitable support materials. An analogous alkylation of tetrazoles and separation of the regioisomers is described, for example, in J. Med. Chem. 1996, 39, 2354.

Compounds of the formula II in which R1, R2 and R3 have the meanings indicated above and R4 is a phenyl radical substituted by a tetrazol-5-yl radical R5, the tetrazol-5-yl radical R5, for its part, being substituted by R6 (R6≠hydrogen), can alternatively also be obtained by a cyclocondensation reaction of the corresponding compounds of the formula III

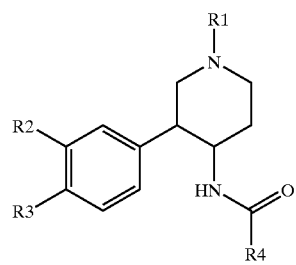

(III)

The cyclocondensation is carried out in a manner known per se to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus trichloride, phosphorus pentoxide, thionyl chloride or preferably phosphorus oxytrichloride, in a suitable inert solvent, e.g. in a chlorinated hydrocarbon such as chloroform, or in a cyclic hydrocarbon such as toluene or xylene, or another inert solvent such as acetonitrile, or without a further solvent using an excess of condensing agent, preferably at elevated temperature, in particular at the boiling temperature of the solvent or condensing agent used.

Enantiomerically pure compounds of the formula II can be separated in a known manner (for example by preparation and separation of corresponding diastereoisomeric compounds) or prepared by stereoselective synthesis methods. Such separation processes and synthesis methods are described, for example in EP 247 971 and in DE 42 17 401.

Compounds of the formula III in which R1, R2, R3 and R4 have the meanings indicated above are accessible from the corresponding compounds of the formula IV

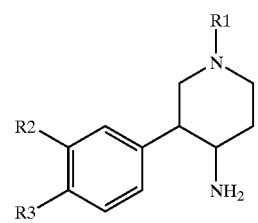

(IV)

in which R1, R2 and R3 have the meanings indicated above, by reaction with compounds of the formula R4-CO-Y in which R4 has the meanings indicated above and Y is a suitable leaving group, preferably a chlorine atom. For example, the benzoylation is carried out as in the following examples according to the Einhorn process, the Schotten-Baumann variant or as described in J. Chem. Soc. (C), 1971, 1805–1808.

Compounds of the formula R4-CO-Y are either known or can be prepared by reaction from the corresponding carboxylic acids R4-COOH in which R4 has the meaning indicated above in a familiar manner to the person skilled in the art.

The compounds R4-COOH in which R4 has the meanings indicated above are either known or can be obtained from alkyl 2-, 3- or 4-cyanobenzoates in a manner known to the person skilled in the art, e.g. by reaction with alkali metal azides and an ammonium halide (e.g. ammonium chloride) to give alkyl 2-, 3- or 4(1H- or 2H-tetrazol-5-yl)benzoates which are unsubstituted in the tetrazole moiety. Such a reaction is described, for example, in J. Med. Chem. 1993, 36, 3246. If desired, these intermediate compounds can be converted—as described above for the 1H- or 2H-tetrazole compounds of the formula II or in the abovementioned literature—by alkylation with compounds of the formula R6-X in the presence of a base, into alkyl R4-carboxylates in which R4 is a phenyl radical substituted by R5, R5 is a 1 H- or 2H-tetrazol-5-yl radical substituted by a radical R6 and R6 is not hydrogen, but has one of the other meanings mentioned for R6. By means of alkaline or acidic hydrolysis conditions familiar to the person skilled in the art, the alkyl R4-carboxylates are converted into the free carboxylic acids R4-COOH.

The preparation of cis/trans racemate mixtures and of pure cis racemates of compounds of the formula IV is described, for example, in U.S. Pat. 3,899,494, in DE-A 21 23 328 and in DE-A 16 95 782. Pure cis-enantiomers of the compounds of the formula IV can be obtained, for example, by the processes such as are described in EP 0 247 971 and in DE 42 17 401.

The substances according to the invention are isolated and purified in a manner known per se, for example by distilling off the solvent in vacuo and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low molecular weight aliphatic alcohol such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically intolerable salts can be converted into pharmacologically tolerable salts.

The following examples serve to illustrate the invention in greater detail without restricting it. Further compounds of the formula I, whose preparation is not explicitly described, can also be prepared in an analagous manner or in a manner familiar per se to the person skilled in the art using customary process techniques.

In the examples, m.p. stands for melting point, h for hour(s), RT for room temperature, EF for empirical formula, MW for molecular weight, TLC for thin-layer chromatography, calc. for calculated, fnd. for found. The compounds mentioned in the examples and their salts are a preferred subject of the invention.

EXAMPLES

Final Products 1. cis-9-Ethoxy-8-methoxy-2-methyl-6-[4-(2H-2-ethyltetrazol-5-yl) phenyl]-1,2,3,4,4a,10b-hexahydrobenzo [c][1,6]naohthyridine N-2-Oxide A solution of 2.23 g of (−)-cis-9-ethoxy-8-methoxy-2-methyl-6-[4-(2H-2-ethyltetrazol-5-yl)phenyl]-1,2,3,4,4a, 10-hexahydrobenzo[c][1,6]naphthyridine (starting compound A) in 12 ml of methanol is stirred at RT for about 2 days with 6 ml of 30% hydrogen peroxide. After oxidation is complete (TLC checking), the reaction mixture is treated with 7 g of solid sodium sulfite and additionally stirred at RT for about 1 h. After filtering the reaction mixture with suction, the filtrate is extracted with dichloromethane, and the organic phase is washed with water and dried over sodium sulfate. After filtering the product solution with suction and concentrating it, the solid residue obtained is crystallized in an ethyl acetate/diethyl ether mixture (2:1). 1.9 g of the title compound are obtained as colorless fine crystals of m.p. 168–170° C.

EF: $C_{25}H_{30}N_6O_3 \times 1.19\ H_2O$; MW: 484.07; Elemental analysis: calc.: C, 62.14 H, 6.74 N, 17.39; fnd.: C, 62.18 H, 7.04 N, 17.44.

Starting Compounds

A. (−)-cis-9-Ethoxy-8-methoxy-2-methyl-6-[4-(2H-2-ethyltetrazol-5-yl)phenyl]-1,2,3,4,4a,10b-hexahydrobenzo [c][1,6]naohthyridine 6.7 g of (−)-cis-3-(3-ethoxy4-methoxyphenyl)4-[4-(2H-2-ethyltetrazol-5-yl)benzamido]-1-methyl-piperidine are heated to boiling under reflux for 16 h in 20 ml of phosphorus oxytrichloride and 80 ml of acetonitrile. After distilling off the excess phosphorus oxytrichloride, the residue is partitioned between dichloromethane and saturated sodium hydrogencarbonate solution. The organic phase is washed with water, dried over sodium sulfate and concentrated. The solid residue is purified by silica gel chromatography, and the main product fraction is separated and concentrated. The residue is recrystallized from petroleum ether/diethyl ether (2:1). 4.6 g of the title compound (pale yellow crystals) of m.p. 151–152° C. are obtained.

EF: $C_{25}H_{30}N_6O_2$, MW: 503.44; Optical rotation: $[\alpha]_D^{20} = -106.4°$ (c=1, methanol).

B. (−)-cis-3-(3-Ethoxy-4-methoxyphenyi)-4-[4-(2H-2-ethyltetrazo]-5-yl )-benzamidol-1-methyl-piperidine A solution of 4-(2H-2-ethyltetrazol-5-yl)benzoyl chloride (prepared by heating 1.5 g of 4-(2H-2-ethyltetrazol-5-yl) benzoic acid under reflux with 2 ml of thionyl chloride in 60 ml of absolute toluene for about 2 h and complete concentration) is added dropwise in the course of 10 min to a solution of 1.82 g of (−)-cis-4-amino-3-(3-ethoxy4-methoxyphenyl)-1-methylpiperidine (free base, prepared by treatment of the dihydrochloride with sodium hydroxide solution and extraction of the free base with dichloromethane) in 60 ml of dichloromethane and 1 ml of triethylamine cooled in an ice/water bath. The reaction mixture is warmed to RT with stirring and additionally stirred for about 2 h. After extraction with a mixture of saturated sodium hydrogencarbonate solution and dichloromethane, the organic phase is completely concentrated and the residue is crystallized in methanol/diethyl ether (1+1). 3.15 g of colorless crystals of the title compound of m.p. 165–167.5° C. are obtained.

EF: $C_{25}H_{32}N_6O_3$, MW: 464.57; Optical rotation: $[\alpha]_D^{20} = -89.7°$ (c=1, methanol); Elemental analysis: calc.: C, 64.64 H, 6.94 N, 18.09. fnd.: C, 64.74 H, 7.08 N, 18.21.

C. (−)-cis4Amino-3-(3-ethoxy-4-methoxyphenyl)-1-methylpiperidine dihydrochloride The title compound is obtained analogously to the process described in DE 42 17 401 for (−)-cis-4-amino-3-(3,4-dimethoxyphenyl)-1-methylpiperidine dihydrochloride if the corresponding 3-ethoxy4-methoxy compounds are employed in the examples described there.

EF: $C_{15}H_{24}N_2O_2 \times 2HCl \times 0.96\ H_2O$, MW: 354.52; m.p. 252–254° C.; Optical rotation: $[\alpha]_D^{20} = -65.5°$ (c=1, methanol).

Commercial Utility

The compounds according to the invention have valuable pharmacological properties which make them commercially utilizable. As selective inhibitors of type 3 and 4 of cyclic nucleotide phosphodiesterase (PDE3, PDE4), they are suitable on the one hand as bronchial therapeutics (for the treatment of airway obstructions on account of their dilating and cilia-stimulating action but also on account of their respiratory rate- and respiratory drive-increasing action), but on the other hand especially for the treatment of disorders of inflammatory nature, e.g. of the airways (asthma prophylaxis), of the skin, of the intestine, of the eyes and of the joints, which are mediated by mediators such as interferons, members of the tumor necrosis factor family, interleukins, chemokines, colony-stimulating factors, growth factors, lipid mediators (e.g., inter alia, PAF, platelet-activating factor), bacterial factors (e.g. LPS), immunoglobulins, oxygen free radicals and related free radicals (e.g. nitrogen monoxide NO), biogenic amines (e.g. histamine, serotonin), kinins (e.g. bradykinin), neurogenic mediators (such as substance P, neurokinin), proteins such as, for example, granular contents of leukocytes (inter alia cationic proteins of eosinophils) and adherent proteins (e.g. integrins). The compounds according to the invention have smooth muscle-relaxant action, e.g. in the region of the bronchial system, of the blood circulation, and of the efferent urinary passages. In addition, they have ciliary frequency-increasing action, e.g. in the bronchial system.

In this context, the compounds according to the invention are distinguished by low toxicity, good human acceptance, good enteral absorption and high bioavailability, great therapeutic breadth, the absence of significant side effects and good water solubility.

On account of their PDE-inhibiting properties, the compounds according to the invention can be employed as therapeutics in human and veterinary medicine, where they can be used, for example, for the treatment and prophylaxis of the following diseases: acute and chronic (in particular inflammatory and allergen-induced) airway disorders of various origin (bronchitis, allergic bronchitis, bronchial asthma, emphysema, COPD); disorders with restriction of the ciliary activity or increased demands on ciliary clearance (bronchitis, mucoviscidosis), dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on excessive release of TNF and leukotrienes, i.e., for example, disorders of the arthritis type (rheumatoid arthritis, rheumatoid spondylitis, osteoarthritis and other arthritic conditions), systemic lupus erythematosus, disorders of the immune system (AIDS), including AIDS-related encephalopathies, autoimmune disorders such as diabetes mellitus (Type I, autoimmune diabetes), multiple sclerosis and of the type virus-, bacteria- or parasite-induced demyelinization diseases, cerebral malaria or Lyme's disease, shock symptoms [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and of the adjacent regions (paranasal sinuses, eyes), such as, for example, allergic rhinitis/sinusitis, chronic rhinitis/sinusitis, allergic conjunctivitis and also nasal polyps; and also disorders of the central nervous system such as memory disorders and Alzheimer's disease, candidiasis, leishmaniases and leprosy.

On account of their vasorelaxant activity, the compounds according to the invention can also be used for the treatment of high blood pressure disorders of various origin such as, for example, pulmonary high blood pressure and the concomitant symptoms associated therewith, for the treatment of erectile dysfunction or colics of the kidneys and the ureters in connection with kidney stones.

On account of their cAMP-increasing action, however, they can also be used for disorders of the heart which can be treated by PDE inhibitors, such as, for example, cardiac insufficiency, and also as antithrombotic, platelet aggregation-inhibiting substances.

The invention further relates to a method for the treatment of mammals including humans who are suffering from one of the abovementioned diseases. The method comprises administering a therapeutically effective and pharmacologically tolerable amount of one or more of the compounds according to the invention to the sick mammal.

The invention further relates to the compounds according to the invention for use in the treatment and/or prophylaxis of diseases, in particular the diseases mentioned.

The invention also relates to the use of the compounds according to the invention for the production of medicaments which are employed for the treatment and/or prophylaxis of the diseases mentioned.

The invention furthermore relates to medicaments for the treatment and/or prophylaxis of the diseases mentioned and which contain one or more of the compounds according to the invention.

A further subject of the invention is a commercial product consisting of a customary secondary packaging, a primary packaging comprising the medicament (for example an ampoule or a blister pack) and, if desired, a pack insert, the medicament exhibiting antagonistic action to cyclic nucleotide phosphodiesterases of type 3 and 4 and leading to the attenuation of the symptoms of diseases which are connected with cyclic nucleotide phosphodiesterases of type 3 and 4, and the suitability of the medicament for the prophylaxis or treatment of diseases which are connected with cyclic nucleotide phosphodiesterases of type 3 and 4 being indicated on the secondary packaging and/or on the pack insert of the commercial product, and the medicament containing one or more compounds of the formula I according to the invention. The secondary packaging, the primary packaging comprising the medicament and the pack insert otherwise correspond to what would be regarded by the person skilled in the art as standard for medicaments of this type.

Advantageously, the substances according to the invention are also suitable for combination with other substances which bring about stimulation of cAMP, such as prostaglandins ($PGE_2$, $PGI_2$ and prostacyclin) and their derivatives, direct adenylate cyclase stimulators such as forskolin and related substances, or substances indirectly stimulating adenylate cyclase, such as catecholamines and adrenergic receptor agonists, in particular beta mimetics. In combination, on account of their cAMP degradation-inhibiting action, they in this case display a synergistic, superadditive activity. This comes to bear, for example, in their use in combination with $PGE_2$ for the treatment of pulmonary hypertension.

The medicaments are prepared by methods known per se and familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the auxiliaries which are suitable for the desired pharmaceutical formulations. Beside solvents, gel-forming agents, ointment bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are administered either directly as a powder (preferably in micronized form) or by atomization of solutions or suspensions which contain them. With respect to the preparations and administration forms, reference is made, for example, to the details in European Patent 163 965.

For the treatment of dermatoses, the compounds according to the invention are used in particular in the form of those medicaments which are suitable for topical application. For the production of the medicaments, the compounds according to the invention (=active compounds) are preferably mixed with suitable pharmaceutical excipients and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.01 and 10 mg per kilogram per day.

Bioloqical Investigations

In the investigation of PDE4 inhibition at the cellular level, the activation of inflammatory cells has particular importance. An example which may be mentioned is the FMLP (N-formylmethionylleucyl-phenylalanine)-induced superoxide production of neutrophilic granulocytes, which can be measured as luminol-potentiated chemoluminescence [McPhail L C, Strum S L, Leone P A and Sozzani S, The neutrophil respiratory burst mechanism. In "Immunology Series" 1992, 57, 47–76; ed. Coffey RG (Marcel Decker, Inc., New York-Basle-Hong Kong)].

Substances which inhibit chemoluminescence and cytokine secretion and the secretion of inflammation-increasing mediators in inflammatory cells, in particular neutrophilic and eosinophilic granulocytes, T-lymphocytes, monocytes and macrophages, are those which inhibit PDE4 or PDE3 and PDE4. The last-mentioned isoenzyme of the phosphodiesterase families is particularly represented in granulocytes. Its inhibition leads to an increase in the intracellular cyclic AMP concentration and thus to the inhibition of cellular activation. PDE4 inhibition by the substances according to the invention is thus a central indicator of the suppression of inflammatory processes. (Giembycz MA, Could isoenzyme-selective phosphodiesterase inhibitors render bronchodilatory therapy redundant in the treatment of bronchial asthma?; Biochem Pharmacol 1992, 43, 2041–2051; Torphy TJ et al., Phosphodiesterase inhibitors: new opportunities for treatment of asthma. Thorax 1991, 46, 512–523; Schudt C et al., Zardaverine: a cyclic AMP PDE3/4 inhibitor. In "New Drugs for Asthma Therapy", 379–402, Birkhauser Verlag Basle 1991; Schudt C et al., Influence of selective phosphodiesterase inhibitors on human neutrophil functions and levels of cAMP and Ca. Naunyn-Schmiedebergs Arch Pharmacol 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press 1996. Hatzelmann A et al., Enzymatic and functional aspects of dual-selective PDE3/4-inhibitors. In "Phosphodiesterase Inhibitors", 147–160, "The Handbook of Immunopharmacology", Academic Press, 1996.

A. Methodology

1. Inhibition of PDE Isoenzymes

The PDE activity was determined according to Thompson et al. (1) with some modifications (2). The test samples contained 40 mM tris HCl (pH 7.4), 5 mM $MgCl_2$, 0.5 $\mu$M cAMP or cGMP, [$^3$H]cAMP or [$^3$H]cGMP (about 50 000 cpm/sample), the PDE isoenzyme-specific additions described in greater detail below, the indicated concentrations of inhibitor and an aliquot of the enzyme solution in a total sample volume of 200 $\mu$l. Stock solutions of the compounds to be investigated in DMSO were prepared in concentrations such that the DMSO content in the test samples did not exceed 1% by volume—to avoid an effect on the PDE activity. After preincubation at 37° C. for 5 minutes, the reaction was started by addition of the substrate (cAMP or cGMP). The samples were incubated at 37° C. for a further 15 min. The reaction was terminated by addition of 50 $\mu$l of 0.2N HCl. After cooling on ice for 10 minutes and addition of 25 $\mu$g of 5'-nucleotidase (snake venom from Crotalus atrox), the mixture was again incubated at 37° C. for 10 min and the samples were then applied to QAE Sephadex A-25 columns. The columns were eluted with 2 ml of 30 mM ammonium formate (pH 6.0). The radioactivity of the eluate was measured and corrected by the corresponding blank values. The proportion of hydrolyzed nucleotide in no case exceeded 20% of the original substrate concentration.

PDE1 ($Ca^{2+}$/calmodulin-dependent) from bovine brain: The inhibition of this isoenzyme was investigated in the presence of $Ca^{2+}$(1 mM) and calmodulin (100 nM) using cGMP as a substrate (3).

PDE2 (cGMP-stimulated) from rat hearts was purified chromatographically [Schudt et al. (4)] and investigated in the presence of cGMP (5 $\mu$M) using cAMP as a substrate.

PDE3 (cGMP-inhibited) and PDE5 (cGMP-specific) were investigated in homogenates of human blood platelets [Schudt et al. (4)] using cAMP or cGMP as a substrate.

PDE4 (cAMP-specific) was investigated in the cytosol of human polymorphonuclear leukocytes (PMNL) [isolated from leukocyte concentrates, see Schudt et al. (5)] using cAMP as a substrate. The PDE3 inhibitor motapizone (1 $\mu$M) was used in order to suppress the PDE3 activity emanating from contaminating blood platelets.

2. Statistics

The $IC_{50}$ values were determined from the concentration-inhibition curves by nonlinear regression using the GraphPad InPlot™ program (GraphPad Software Inc., Philadelphia, USA).

3. References (1) Thompson W. J., Terasaki W. L., Epstein P. M. and Strada S. J., Assay of cyclic nucleotide phosphodiesterase and resolution of multiple molecular forms of the enzyme; Adv. Cycl. Nucl. Res. 1979, 10, 69–92

(2) Bauer A. C. and Schwabe U., An improved assay of cyclic 3',5'-nucleotide phosphodiesterase with QAE Sephadex A-25; Naunyn-Schmiedeberg's Arch. Pharmacol. 1980, 311, 193–198

(3) Gietzen K., Sadorf I. and Bader H., A model for the regulation of the calmodulin-dependent enzymes erythrocyte Ca2+-transport ATPase and brain phosphodiesterase by activators and inhibitors; Biochem. J. 1982, 207, 541–548

(4) Schudt C., Winder S., Müller B. and Ukena D., Zardaverine as a selective inhibitor of phosphodiesterase isoenzymes; Biochem. Pharmacol. 1991, 42, 153–162

(5) Schudt C., Winder S., Forderkunz S., Hatzelmann A. and Ullrich V., Influence of selective phosphodiesterase inhibitors on human neutrophil functions and levels of cAMP and Ca; Naunyn-Schmiedeberg's Arch. Pharmacol. 1991, 344, 682–690

B. Results

In Table 1 below, the inhibitory concentrations determined according to Section A1 [inhibitory concentrations as $-\log IC_{50}$ (mol/l)] for compound 1 are indicated for various PDE isoenzymes. The number of the compound corresponds to the number of the example in the final products section.

TABLE 1

| Compound | PDE4 [-log $IC_{50}$, mol/l] | PDE3 |
|---|---|---|
| 1 | 7.53 | 6.11 |

What is claimed is:
1. A compound of the formula I,

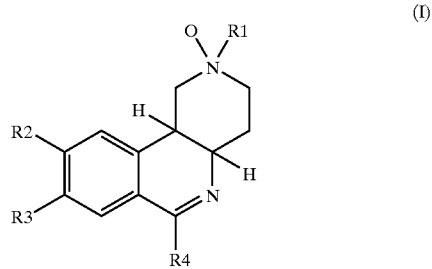

(I)

in which
R1 is 1–4C-alkyl,
R2 is hydroxyl, 1–4C-alkoxy, 3–7C-cycloalkoxy, 3–7C-cycloalkylmethoxy or 1–4C-alkoxy which is completely or predominantly substituted by fluorine,
R3 is hydroxyl, 1–4C-alkoxy, 3–7C-cycloalkoxy, 3–7C-cycloalkylmethoxy or 1–4C-alkoxy which is completely or predominantly substituted by fluorine,
or in which
R2 and R3 together are a 1–2C-alkylenedioxy group,
R4 is a phenyl radical which is substituted by R5, where
R5 is a tetrazol-5-yl radical which is substituted by a radical R6, where
R6 is hydrogen, 1–10C-alkyl, 3–7C-cycloalkyl, 3–7C-cycloalkylmethyl or Ar-1–4C-alkyl,
where
Ar is a phenyl radical which is unsubstituted or substituted by R7 and/or R8, and
R7 and R8 independently of one another are 1–4C-alkyl or 1–4C-alkoxy,
or a salt thereof.

2. A compound of the formula I as claimed in claim 1, in which
R1 is 1–2C-alkyl,
R2 is 1–4C-alkoxy, 3–7C-cycloalkoxy, 3–7C-cycloalkylmethoxy or 1–4C-alkoxy which is completely or predominantly substituted by fluorine,
R3 is 1–4C-alkoxy, 3–7C-cycloalkoxy, 3–7C-cycloalkylmethoxy or 1–4C-alkoxy which is completely or predominantly substituted by fluorine,
or in which
R2 and R3 together are a 1–2C-alkylenedioxy group,
R4 is a phenyl radical which is substituted by R5, where
R5 is a tetrazol-5-yl radical which is substituted by a radical R6, where
R6 is hydrogen, 1–7C-alkyl, 3–7C-cycloalkyl, 3–7C-cycloalkylmethyl or Ar-1–4C-alkyl,
where
Ar is a phenyl radical which is unsubstituted or substituted by R7 and/or R8, and
R7 and R8 independently of one another are 1–4C-alkyl or 1–4C-alkoxy,
or a salt thereof.

3. A compound of formula I as claimed in claim 1, in which
R1 is methyl,
R2 is 1–4C-alkoxy, 3–7C-cycloalkoxy, 3–7C-cycloalkylmethoxy or 1–2C-alkoxy which is completely or predominantly substituted by fluorine,
R3 is 1–4C-alkoxy, 3–7C-cycloalkoxy, 3–7C-cycloalkylmethoxy or 1–2C-alkoxy which is completely or predominantly substituted by fluorine,
R4 is a phenyl radical which is substituted by R5, where
R5 is a tetrazol-5-yl radical which is substituted by a radical R6, where
R6 is hydrogen, 1–7C-alkyl, 5–7C-cycloalkyl, 3–7C-cycloalkylmethyl or Ar-1–2C-alkyl,
where
Ar is a phenyl radical which is unsubstituted or substituted by R7, and
R7 is 1–2C-alkyl or 1–2C-alkoxy,
or a salt thereof.

4. A compound of formula I as claimed in claim 1, in which
R1 is methyl,
R2 is 1–4C-alkoxy,
R3 is 1–4C-alkoxy,
R4 is a phenyl radical which is substituted by R5, where
R5 is a tetrazol-5-yl radical substituted by a radical R6, where
R6 is hydrogen, 1–7C-alkyl, cyclohexylmethyl or 4-methoxybenzyl,
or a salt thereof.

5. A compound of formula I as claimed in claim 1, in which
R1 is methyl,
R2 is ethoxy,
R3 is methoxy or ethoxy,
R4 is a phenyl radical which is substituted by R5, where R5 is a tetrazol-5-yl radical substituted by a radical R6, where R6 is 1–4C-alkyl, or a salt thereof.

6. A compound of formula I as claimed in claim 1, in which the hydrogen atoms in positions 4a and 10b are in the cis position relative to one another, or a salts thereof.

7. A compound of formula I as claimed in claim 1, which in the positions 4a and 10b have the same absolute configuration as the compound (−)-cis-4-amino-3-(3-ethoxy4-methoxyphenyl)-1-methylpiperidine dihydrochloride having the optical rotation $[\alpha]_D^{20}$=−65.5° (c=1, methanol), which can be employed as a starting material.

8. A composition comprising one or more compounds as claimed in claim 1 together with the customary pharmaceutical excipients and/or vehicles.

9. A method for compounding a pharmaceutical composition by combining an active ingredient for treating an airway disorder and/or a dermatosis with a customary pharmaceutical excipient and/or vehicle, wherein the active ingredient is a compound as claimed in claim 1 or a pharmacologically acceptable salt thereof.

10. A method of treating a subject afflicted with a high blood pressure disorder which comprises administering to the subject an effective amount of a compound as claimed in claim 1 or a pharmacologically acceptable salt thereof.

* * * * *